United States Patent [19]

Hamilton et al.

[11] Patent Number: 4,926,795

[45] Date of Patent: May 22, 1990

[54] METHOD OF REINSTATING ACCEPTABLE FLAVOR TO OFF-FLAVOR CATFISH BY TREATMENT WITH PEROXIDE ADDITIVES

[75] Inventors: Frank S. Hamilton, Schlater; Johnny D. Ouzts, Cleveland; Ray W. Mabry, Greenwood, all of Miss.

[73] Assignee: HOM, Inc., Greenwood, Miss.

[21] Appl. No.: 309,869

[22] Filed: Feb. 14, 1989

[51] Int. Cl.$^5$ ............................................... A01K 61/00
[52] U.S. Cl. ......................................................... 119/3
[58] Field of Search ................................. 119/3; 426/2

[56] References Cited

U.S. PATENT DOCUMENTS

| | | |
|---|---|---|
| 2,245,495 | 6/1941 | Pemble . |
| 3,514,278 | 5/1970 | Brink ........................................ 71/67 |
| 3,684,477 | 8/1972 | Blumberg ................................. 71/67 |
| 4,398,937 | 8/1983 | Van Aller et al. ....................... 71/67 |

FOREIGN PATENT DOCUMENTS

| | | | |
|---|---|---|---|
| 2911208 | 10/1980 | Fed. Rep. of Germany | 71/67 |
| 49-27799 | 7/1974 | Japan | 119/3 |
| 141142 | 11/1980 | Japan | 119/3 |
| 2278104 | 12/1987 | Japan | 119/3 |
| 1294314 | 3/1987 | U.S.S.R. | 119/3 |

OTHER PUBLICATIONS

Kay, S. H., Quimby, P. C., Jr. and Ouzts, J. D., "H$_2$O$_2$: A Potential Algicide for Aquaculture", New Perspectives in Weed Science, pp. 275–289 (1982).
Quimby, P. C., Jr., and Kay, S. H., "Sodium Carbonate Peroxyhydrate as a New Algicide", Aquatic and Marginal Weeds, Section V, (1984).
Marathe, V. B., Huilgol, N. V., and Path, S. G., "Hydrogen Peroxide as a Source of Oxygen Supply in the Transport of Fish Fry", Progressive Fish–Culturist, vol. 37, No. 2, p. 117 (1975).
Balvay, G., "Biological Consequences of Treating a Lake with Hydrogen on the Plankton Biocenosis", vol. 15, pp. 691–969 (1981).
Lovell, R. T. and Sackey, L. A., "Absorption by Channel Catfish of Earthy-Musty Flavor Compounds Synthesized by Cultures of Blue-Green Algae", Trans. Amer. Fish Soc., vol. 102, pp. 774–777 (1973).
Quimby, P. C., Kay, S. H., and Ouzts, J. D., "Sodium Carbonate as a Potential Algicide", J. Aquatic Plant Manage., 26, pp. 67–68 (1987).
Boyd, C. E., "Water Quality in Fish Ponds", Agric. Exp. Stn., Auburn University, pp. 61–64 (1979).
Lovell, R. T., "The Off-Flavor Problem in Commercially Cultured Catfish", 68th Meeting of Association of Southern Agricultural Workers, Inc., p. 139 (1971).

*Primary Examiner*—Robert P. Swiatek
*Attorney, Agent, or Firm*—Larson and Taylor

[57] ABSTRACT

A method of reinstating acceptable flavor to catfish determined to have an unacceptable earthy, musty flavor comprising treating an aquaculture with an inorganic peroxide which releases hydrogen peroxide into the aquatic environment, and subjecting the fish to the treated environment for a time sufficient to reinstate acceptable flavor. Hydrogen peroxide itself or inorganic peroxide which release hydrogen peroxide, such as sodium percarbonate peroxyhydrate, may be used. Flavor reinstatement is achieved in as little as 72 hours.

7 Claims, No Drawings

METHOD OF REINSTATING ACCEPTABLE FLAVOR TO OFF-FLAVOR CATFISH BY TREATMENT WITH PEROXIDE ADDITIVES

BACKGROUND OF THE INVENTION

The invention relates to a method of treating living non-scaly fish, such as catfish, which have been determined to have an earthy, musty taste ("off"-flavor) to restore an acceptable fish flavor. This invention relates more particularly to flavor reinstatement of catfish in commercial catfish ponds found to contain off-flavor catfish.

As of October, 1988, the official total acreage of catfish ponds in Mississippi was 93,700. This acreage has a production potential of in excess of 200 million pounds of catfish. A major problem in the catfish industry is that suitable techniques have not been available for the establishment of acceptable fish flavor in accordance with market requirements.

An effective method of flavor reinstatement has important commercial consequences, since the loss of a considerable investment of effort (towards cultivating catfish to adulthood) resulting from the presence of the unwanted off-flavor in the fish may be avoided. A 1972 survey of several large scale processors reported that over 50% of ponds tested at harvesting time contained fish with such intense off-flavor that harvesting was postponed until flavor improved.

Both off-flavor catfish and insufficient algae management individually result in significant losses in the industry; however, the problems are somewhat interrelated. The presence in the pond of some algal species, especially blue-green algae, imparts an earthy-musty odor and flavor to the fish and aquatic environment. Most off-flavor problems in harvested fish have been attributed to the blue-green species of algae, which are commonly found in dense blooms in fish culture ponds.

A previous approach (U.S. Pat. No. 4,398,937) involving use of the algicide ricinoleic acid to restore acceptable fish flavor, has several drawbacks. Flavor reinstatement is achieved after addition of this fatty acid species to off-flavor fish after a lengthy period of 13 days. Further, addition of a fatty acid compound into the delicately balanced aquatic environment can have negative affects, such as fish weight loss, and toxic effects on non-target species (arthropods, etc.), all of which may result in a disturbed, less productive ecosystem.

Lovell and Sackey approached the flavor problem by introducing off-flavor fish into a flowing, charcoal filtered water, and found that flavor improved after three days and that complete flavor restoration occurred in 10 days. *Trans American Fish Soc.*, (1973) Vol. 102, p. 774–777. This type of treatment has the disadvantages of being both costly and time consuming to employ.

SUMMARY OF THE INVENTION

It has been found in accordance with this invention that an aquatic environment containing non-scaly fish determined to be off-flavor may be safely treated with an inorganic peroxide which releases hydrogen peroxide into the aquatic environment so as to achieve flavor reinstatement of such fish within as little as about 72 hours. The method offers several advantages over the prior art, by being both safe and fast-acting.

The present invention meets a range of safety criteria established for use of chemicals in aquacultural applications. In particular, experiments of addition of $H_2O_2$ to laboratory and field aquacultures have determined that at levels of not more than about 33 ppm, $H_2O_2$ is relatively non-toxic to catfish of various sizes. Toxicity tests performed with a preferred hydrogen peroxide-liberating additive, sodium carbonate peroxyhydrate (SCP), verified its a safety to catfish fingerlings (fish size less than 5 inches long).

Hydrogen peroxide, upon contact with water degrades rapidly into two naturally occurring elements in catfish ponds: water and oxygen. It is contemplated that hydrogen peroxide itself or a variety of other inorganic hydrogen peroxide liberating compounds, in addition to SCP may be used as well. Examples of such compounds which release hydrogen peroxide in an aqueous medium may include the alkali and alkaline earth metal salts, such as sodium and potassium percarbonates, perborates, persilicates, orthophosphate perhydrates, pyrophosphate perhydrates, polyphosphate perhydrates and sulfate perhydrates. It is contemplated that alkali and alkaline earth metal peroxides may be used as well, such as sodium peroxide, potassium peroxide, calcium peroxide and zinc peroxide. These inorganic compounds may be peroxide salts which liberate (or generate) hydrogen peroxide by reaction with water, or they may be crystalline compounds holding hydrogen peroxide within their structure which is released when the compound is mixed with water. In the present specification and claims the term "inorganic peroxide" is intended to include $H_2O_2$ itself, as well as the above salts which liberate $H_2O_2$ in water.

The compound sodium carbonate peroxyhydrate (SCP), of formular $2Na_2CO_3 \cdot 3H_2O_2$ is a preferred inorganic peroxide which is employed in the present method. Applied as a solid, SCP provides both ease of application and allows stable measurements of concentration to be taken. Aqueous $H_2O_2$ is also suitable and is widely commercially available in various concentrations. If aqueous $H_2O_2$ is used, its concentration is preferably not more than 35% by weight and more preferably not more than 5 or 10% by weight when added to the aquatic improvement.

Addition of hydrogen peroxide to an aquaculture suppresses many algal species, including Actinomycetes, and blue-green algal species such as *Microcystis, Anaebena, Raphidiopsis* and *Ankistrodesmus*. Heavy concentrations of odor-producing Actinomycetes and blue-green algae found in ponds with off-flavor catfish are suspected of being organisms responsible for imparting the off-flavor to the fish.

A practical advantage of the safety of hydrogen peroxide use in the present method is that the effluent from commercial catfish ponds which have been so treated may be used for crop irrigation. Hydrogen peroxide has been shown to stimulate seed germination of rice and has been shown to have no adverse effects on vegetative and seedling growth of rice, corn, soybeans, tomatoes, pigweed or barnyard grass.

A very important advantage of the method is the expedience with which flavor reinstatement occurs. It is readily possible to achieve flavor reinstatement in as little as 72 hours in accordance with the invention. The rate at which flavor is reinstated is believed to be in part dependent upon the amount of hydrogen peroxide released into the aquatic environment.

To achieve expedient flavor reinstatement, inorganic peroxide should be added such that about 3 to 80 lbs. of active hydrogen peroxide, preferably about 5–65 lbs., more preferably about 10–55 lbs., are released per acre of aquatic environment. The term "aquatic environment" in the present specification and claims is considered to mean any pond, raceway or like aquaculture which is on average at least one foot deep. Commercially, SCP will typically release about 27% by weight $H_2O_2$. Thus, the amount of commercial SCP that is needed to achieve such $H_2O_2$ release is about 10 to 300 lbs. per surface acre of aquatic environment.

Additionally, an advantage of the use of hydrogen peroxide in the method is its minimal effect on other pond life. Experiments performed on crayfish, dragonfly naiads and fly larvae indicated that these organisms are highly tolerant to peroxide applied in amounts commensurate with the method described herein.

A preferred means of employing the method is to apply the inorganic peroxide directly to the catfish pond containing off-flavor fish in such a manner that the compound is widely, and preferably substantially uniformly, distributed over the surface of the pond. Any conventional application method may be used, such as spraying the pond with a liquid or by dispensing a particulate material from a boat. While the inorganic peroxide will ordinarily be added to an aquatic environment in which the off-flavor fish are present, one may first treat an aquaculture, such as a pond, tank or raceway with an inorganic peroxide, and subsequently add the fish to the environment to reinstate flavor.

The following examples serve serve to illustrate the method in more detail.

EXAMPLE I

FIELD EXPERIMENT

To determine the effect of SCP on catfish flavor, a one-acre man-made pond used for commercial catfish containing off-flavor catfish is selected for testing. Pond dimensions are calculated to be 0.9 acre surface area, and depth of 3–6 feet (sloped bottom). The sloped bottom is a typical construction feature of such ponds, and assists in harvesting.

Prior to application of SCP, random fish samples are taken from the pond using the hook and line method. The samples of caught fish are taken into the laboratory, rinsed in tap water, and their heads and organs removed. The fish are then cooked (unseasoned) individually in a microwave until "done" (about 6 minutes, depending on the size of the fish). Taste determination by a technician trained to determine if flavor was "on" (acceptable) or "off" (earthy, musty) is then performed. Alternatively, one may use a scale of 1 to 10 to indicate taste ranging from intensely off-flavor to no-off flavor, respectively. Only edible portions are tasted. A taste analysis of fish samples from the commercial pond is performed, and the fish are determined to be off-flavor.

100 lbs. of dry SCP is applied to the pond containing off-flavor catfish by dispersion from a Jon Boat. Application is made downwind to allow the wind's effect on wave action to mix the SCP without mechanical means. The pond contains catfish, which on average were of harvestable size (1.5–3 lbs.). The number of catfish contained in such a commercial pond may vary from 2000–25,000/acre, and in this pond is about 5000/acre.

After treatment of the pond with 100 lbs. SCP as described, fish samples are taken using the hook and line method at intervals of 24, 48, 72, 96 and 120 hours. Acceptable on-flavor is confirmed by an unbiased technician in slightly over 72 hours after treatment. No significant fish mortality occurs during treatment or in the 120 hour period thereafter. The resulting on-flavor fish in the pond are thus rendered acceptable for harvest and sale 72 hours after treatment with SCP.

EXAMPLE II

TANK TEST

In this example, two 75-gallon tanks are set up, each to contain six off-flavor catfish in 50 gallons of off-flavor pond water. Fish from the pond water source are determined to be off-flavor by an unbiased technician.

After filling the tanks with off-flavor pond water, but prior to introduction of catfish, 12g of SCP are added to one tank to give a concentration of 17 ppm $H_2O_2$. The second tank, a control, receives no SCP. Within one hour, 6 catfish weighing approximately 1.5 lbs. each are introduced into both treated and untreated tanks. Both tanks were equipped with aerators to simulate cultural conditions.

After 24 hours, one fish specimen is removed from each tank and flavor-tested. There is no flavor change in either fish. After 72 hours, tests for flavor reinstatement are conducted by the same technician. Satisfactory results are gained in the SCP treated fish, but the control remained off-flavor.

Further tests using the same procedure with new pond water each time and the same treatment/control procedure yield similar results after about 72 hours.

Further testing following the described procedure for treatment and fish introduction are conducted with SCP at a level of 11.5 ppm $H_2O_2$. Flavor reinstatement is achieved from 72 to 96 hours. In all tests for all rates, there is no mortality. This indicates a very high degree of safety.

We claim:

1. A method of achieving commercially acceptable flavor reinstatement in non-scaly fish intended to be marketed commercially, said fish having been determined to have a commercially unacceptable off-flavor comprising:
   incorporating an inorganic peroxide into an aquatic environment to release hydrogen peroxide into said aquatic environment, and
   subjecting said off-flavor fish to said aquatic environment for a time sufficient to reinstate commercially acceptable fish flavor.

2. The method of claim 1 wherein said inorganic peroxide comprises sodium carbonate peroxhydrate and, wherein the amount of said sodium carbonate peroxyhydrate incorporated into said aquatic environment is about 10 to 300 lbs. per acre.

3. The method of claim 1 wherein said inorganic peroxide comprises $H_2O_2$.

4. The method of claim 1 wherein the amount of inorganic peroxide incorporated in said aquatic environment is such that the amount of hydrogen peroxide released into said aquatic environment is about 3 to 80 pounds per acre of said aquatic environment.

5. The method of claim 4 wherein the said amount of hydrogen peroxide released is about 5 to 65 pounds per acre.

6. The method of claim 4 wherein said amount of hydrogen peroxide released is about 10 to 55 pounds per acre.

7. A method of achieving commercially acceptable flavor reinstatement in non-scaly fish raised in an aquatic environment and intended to be marketed commercially, said fish having been determined to have a commercially unacceptable off-flavor comprising:
  subjecting said off-flavor fish in said aquatic environment to an effective amount of an inorganic peroxide which releases hydrogen peroxide into said aquatic environment for a time sufficient to reinstate commercially acceptable flavor.

* * * * *